United States Patent [19]

Heikkilä et al.

[11] Patent Number: 5,770,061
[45] Date of Patent: Jun. 23, 1998

[54] CHROMATOGRAPHIC SEPARATION COLUMN, INNER STRUCTURES THEREOF, AND CHROMATOGRAPHIC SEPARATION

[75] Inventors: Heikki Heikkilä, Espoo; Göran Hyöky; Jarmo Kuisma, both of Kantvik, all of Finland

[73] Assignee: Suomen Sokeri Oy, Helsinki, Finland

[21] Appl. No.: 909,516

[22] Filed: Aug. 12, 1997

Related U.S. Application Data

[63] Continuation of Ser. No. 583,202, Jan. 4, 1996, abandoned, which is a continuation of Ser. No. 184,615, Jan. 21, 1994, abandoned.

[30] Foreign Application Priority Data

Jan. 25, 1993 [FI] Finland .................................. 930297

[51] Int. Cl.$^6$ .................................................. B01D 15/08
[52] U.S. Cl. .......................... 210/198.2; 210/656; 97/107
[58] Field of Search .............................. 210/656, 198.2, 210/283, 284, 285, 286; 261/94, 112.1, 112.2; 96/107, 152, 154

[56] References Cited

U.S. PATENT DOCUMENTS

| | | | |
|---|---|---|---|
| 1,402,147 | 1/1922 | Day .................................... | 261/112.2 |
| 1,823,269 | 9/1931 | Grilli .................................. | 261/112.2 |
| 2,845,136 | 7/1958 | Robinson .......................... | 96/107 |
| 3,070,937 | 1/1963 | Bub .................................... | 96/154 |
| 3,132,190 | 5/1964 | Engalitcheff ...................... | 261/112.2 |
| 3,227,429 | 1/1966 | Renzi .................................. | 261/112.1 |
| 3,230,167 | 1/1966 | Golay ................................. | 96/107 |
| 3,250,058 | 5/1966 | Baddour ............................ | 96/107 |
| 3,298,527 | 1/1967 | Wright ............................... | 210/198.2 |
| 3,316,064 | 4/1967 | Kuzuoka ........................... | 261/112.2 |
| 3,374,606 | 3/1968 | Baddour ............................ | 96/107 |
| 3,398,512 | 8/1968 | Perkins .............................. | 96/107 |
| 3,407,574 | 10/1968 | Perkins ............................ | 210/283 |
| 3,436,897 | 4/1969 | Crowley ........................... | 96/107 |
| 3,453,811 | 7/1969 | Crowley ........................... | 96/107 |
| 3,493,497 | 2/1970 | Pretorius ........................... | 210/198.2 |
| 3,494,103 | 2/1970 | Mir .................................... | 96/107 |
| 3,522,172 | 7/1970 | Pretorius ........................... | 210/198.2 |
| 3,539,505 | 11/1970 | Lauer et al. .................... | 55/67 |
| 3,566,611 | 3/1971 | Sterrett ............................. | 210/283 |
| 3,626,666 | 12/1971 | Drinkard ......................... | 96/107 |
| 3,657,864 | 4/1972 | Davis ................................ | 55/386 |
| 3,796,657 | 3/1974 | Pretorius ........................... | 210/198.2 |
| 4,208,284 | 6/1980 | Pretorius ........................... | 210/198.2 |
| 4,259,186 | 3/1981 | Boeing .............................. | 210/198.2 |
| 4,557,830 | 12/1985 | Onitsuka ......................... | 210/198.2 |
| 4,604,199 | 8/1986 | Yoritomi .......................... | 210/293 |
| 4,636,315 | 1/1987 | Allen ................................. | 96/152 |
| 4,732,687 | 3/1988 | Muller .............................. | 210/198.2 |
| 4,976,865 | 12/1990 | Sanchez .......................... | 210/198.2 |
| 5,032,156 | 7/1991 | Luder et al. .................... | 55/269 |
| 5,124,133 | 6/1992 | Schoenrock ..................... | 210/286 |
| 5,204,027 | 4/1993 | Armstrong ...................... | 261/112.2 |
| 5,267,444 | 12/1993 | Lehman .......................... | 261/112.2 |

FOREIGN PATENT DOCUMENTS

| | | | |
|---|---|---|---|
| 0 005 708 | 12/1979 | European Pat. Off. .......... | 210/198.2 |
| 383.263 | 3/1976 | Sweden ........................ | 210/198.2 |
| 1403382 | 8/1975 | United Kingdom .............. | 210/198.2 |

*Primary Examiner*—Ernest G. Therkorn
*Attorney, Agent, or Firm*—Kenyon & Kenyon

[57] ABSTRACT

The invention relates to a chromatographic separation column whose filling material space comprises in the vertical direction at least two zones between which no means that would hinder vertical flow exist and which are divided by means of substantially vertical walls into separate sections. These zones are so dimensioned that the upper edge of the walls in the uppermost zone is below the upper surface of the column filling material in the operating conditions of the column. The invention further relates to inner structures for such a column and to a chromatographic method for separating dissolved constituents by means of said separation column. In this method, a solution is fed alternately with an eluent uniformly across the upper surface of the filling material in the separation column, the solution is allowed to flow through the filling material bed, and the fractions containing the desired products are collected from the liquid flow passed through the filling material.

14 Claims, 5 Drawing Sheets

TESTS 1-2 WITHOUT INNER STRUCTURE (D = 3.6 m)
TESTS 3-5 WITH INNER STRUCTURE (D = 3.6 m)
TESTS 6 WITHOUT INNER STRUCTURE (D = 2.76 m)

CHROMATOGRAPHIC SEPARATION COLUMN, INNER STRUCTURES THEREOF, AND CHROMATOGRAPHIC SEPARATION

This application is a continuation of application Ser. No. 08/583,202, filed on Jan. 4, 1996, which is a continuation of application Ser. No. 08/184,615, filed Jan. 21, 1994, both now abandoned.

The present invention relates to a chromatographic separation column provided with inner structures improving the efficiency of the column and the separation result. Such inner structures, to which the invention also relates, are particularly suitable for use in large columns in which the diameter is in excess of about 1.5 m and the height of the filling material in the column several meters. The invention also relates to a chromatographic separation method employing such a column.

When chromatographic separation methods are used on an industrial scale in large separation columns, a number of difficulties arise. When the column is filled with a slurry of filling material and the filling material has been allowed to settle, the filling is flush and its surface will assume a certain height. When eluent is subsequently conveyed through the filling material, the surface of the filling material will initially lower intensely during a few hours, and thereafter during the processing of the material to be separated, the surface of the filling material will drop further during a few days. The pressure difference over the height of the filling bed increases sharply at the beginning of the process, whereafter the increase is slowed down. When the process is continued for several days in such a way that water and material to be separated are alternately conveyed through the filling material, the dry solids concentration of the product fractions diminishes and their purity decreases; simultaneously the separation capacity of the column diminishes. As the separation result and column capacity are no longer adequate, the processing must be discontinued, and re-packing of the filling material must be effected. The filling material is backwashed, in which connection water is conveyed therethrough from bottom to top at a high velocity. Then the filling material bed is expanded and fluidized. Thereafter the filling material is allowed to settle, and subsequently the separation process can be restarted.

The compacting of the filling material during the separation process is harmful, since it has an effect of decreasing the separation capacity. The non-uniform compacting of the filling material is detrimental, causing channeling of the liquid flow. In that case, the concentration profile of the material to be separated in the cross-section of the column, in other words the fronts, does not remain uniform, and the separation result is impaired. This is manifested in the fact that the elution diagrams for the different components, which in the ideal case are relatively steep Gaussian curves, flatten out and may become entirely irregular.

The above drawbacks are enhanced as the column diameter and bed height increase. The harmful effect of the increase in diameter is manifested even with relatively small columns; for instance in a chromatographic column with a diameter of about 25 cm, the compacting is substantially slower than in a column with a diameter of 1 m. The same effect continues when the diameter of the column is further increased, and the difference is clearly seen in the separation of sucrose and betaine from molasses in columns having a diameter of 3.6 m and 2.76 m respectively.

Various constructions to be fitted within columns are known, wherewith attempts have been made to diminish the above drawbacks.

By providing the column with plates which are permeable to the liquid flow but carry the filling material, the filling material can be divided into several superimposed layers, thus diminishing the pressure difference over the total height of the filling material. For example British Patent No. 1,203,439 (Pharmacia Fine Chemicals AB) discloses such a construction for use in a gel filtration column, wherein the filling bed is divided by liquid-permeable plates into several mutually separated superimposed sections. In that case however the separation result is impaired, and the filling of the column with filling material, the backwashing of said filling material, and the removal of spent filling material is considerably impaired. A solution of the same type is disclosed in U.S. Pat. No. 3,539,505 (Lauer, K. and Stoeck, G.; assignors to Boehringer Mannheim GmbH); this solution is stated to enable improvement of the separation result. According to this publication, the filling bed is divided in the longitudinal direction of the column into separation zones, between which relatively shallow mixing zones defined by plates permeable to the liquid flow and containing no filling material are provided. In the mixing zones, a movement diverging from the axial direction of the column is imparted to the liquid. When the liquid leaves such a mixing zone, its front is in fact uniform. Yet the mixing zone does not correct the non-uniformity and flattening out of the front, which originated in the area of the preceding separation zone. This construction thus does not give a sufficiently good separation result either, and further has the drawback that column filling and emptying and re-packing of the filling material is difficult.

Attempts have also been made to eliminate the disadvantages of large columns by means of various walls disposed in the column and having the direction of the vertical axis of the column. These walls divide the column into several parallel sections of a smaller cross-section, said sections extending continuously throughout the filling bed or throughout almost the entire bed. Such constructions are described in European Published Application 5708 (Röhm GmbH), according to which the column can be divided by means of vertical concentric cylindrical walls into sections, the central section being circular and the encircling sections annular in cross-section. In another construction according to this publication, the column is divided, by means of vertical walls at right angles to each other, into sections having a rectangular cross-section. These constructions are so configured that the upper ends of the walls remain beneath the upper surface of the filling material, on account of which the upper surface of the filling material is substantially uniform and flush. It is maintained in the publication that constructions of this kind reduce compaction of the column-filling material. There are, however, differences in the passage rate of the front. On account of the different geometries of the different sections, different compacting of the sections is possible, and thus the combined product removed from the different sections is inadequate.

Also U.S. Pat. No. 5,124,133 (Wilmer Schoenrock) discloses columns in which constructions formed by plates vertically extending continuously through the filling bed are provided. These constructions are claimed to effect flow straightening by preventing lateral flow, so that an uniform flow profile is produced. The plates can segregate the column into different sections, so that a cylindrical section is provided at the center of the column, and the space between said cylinder and the wall of the column is further divided into sections by means of radially oriented plates. Also in this case, however, the passage rates of the front may be different in different sections and hence the separation result may be poor. This publication also discloses a construction in which two series of vertical plates extending throughout the height of the filling bed are installed in the column. One of said series is secured radially and equidistantly to a vertical post provided at the center of the column, and the plates of the other series are secured to the wall of the column and extend inwardly in the radial direction of the column between the plates of the first series. The width of the plates in each series is somewhat greater than half of the distance between the vertical post and the column wall. Since this construction has relatively long unsupported plate edges within the filling material and the filling material can present very large local pressure differences, such constructions must be rather heavy in order for the plates to remain straight. Arranging such a construction in a large column is therefore difficult.

U.S. Pat. No. 3,298,527 discloses a chromatographic separation column provided with a plurality of fin members mounted on the inner wall of the column and extending inwardly and longitudinally therethrough. The column according to said patent may also consist of identical segments in an end-to-end relationship, each segment containing such fin members and being rotated relative to the segments adjacent to it so that the fins in two adjacent segments are not angularly aligned. If such a column were scaled up for use in industrial separation processes, the same drawbacks as described above in connection with the construction according to U.S. Pat. No. 5,124,133 would appear.

It has now been found that the capacity and separation result of large separation columns can be markedly improved by arranging in the column an inner structure different from those known previously. This inner structure is light, self-supporting and easy to install in the column. Accordingly, the present invention relates to a separation column which is characterized in that its filling material space comprises in the vertical direction at least two zones between which no means that would hinder vertical flow exist and which are divided by means of substantially vertical walls into separate sections, the zones being so dimensioned that the upper edge of the walls in the uppermost zone is below the upper surface of the column filling material in the operating conditions of the column.

The walls of two superimposed zones are so arranged as to be offset from one another.

The walls form a cell structure in each zone. It is important that the walls in the structure do not form angles substantially smaller than 90° with one another and with the column wall, since in such corners the compacting of the filling material and the liquid flow could deviate from those prevailing in the other regions of the section and thereby impair the separation result.

Preferably the walls included in each zone form a cell structure in which the walls adjoin one another at an angle of 120° and the column wall in the radial direction of the column. In such a preferred construction, each zone thus comprises at least one section having a cross-section of a substantially equilateral hexagon. In this case, the cell structures of two superimposed zones are so arranged that the straight lines at which the walls of a specific zone adjoin one another are in the middle of the sections of the following zone.

The structure according to the invention is particularly suitable for use in columns having a diameter of from 1 to 5 m, preferably from 2 to 4 m. The combined height of the zones is preferably about 70–90% of the height of the filling bed in the column, and each zone may be from 0.5 to 3 m in height, preferably from 1 to 2 m. Suitable diameters for the sections are naturally dependent on the diameter of the column and are preferably from about 0.25 to about 1.5 m, most preferably from about 0.5 to about 1 m.

Successive zones may contact one another, or spaces with no wall structures may be provided between them. Such a space with no wall structures must, however, be comparatively low relative to the height of the zone, at the most about 10% of the height of the zone.

On account of the inner structure described above, the filling material (stationary phase) will not be non-uniformly compacted, and the packing of the column will remain substantially uniform at different points of the column. The inner structure will maintain the filling material homogeneous for a longer time after backwashing, and compacting is not as intense as without said inner structure.

The invention thus also relates to an inner structure to be arranged in a separation column, diminishing and/or balancing the compacting of the filling material, being characterized in that it forms at least two zones in the filling material space of the column in the vertical direction, between which zones no means that would hinder vertical flow exist and which are divided by means of substantially vertical walls into separate sections, the zones being so dimensioned that the upper edge of the walls in the uppermost zone is below the upper surface of the column filling material in the operating conditions of the column. The walls of two superimposed zones are so arranged as to be offset from one another.

The invention also relates to a chromatographic method for separating dissolved constituents in a solution. This method is characterized in that said solution is fed alternately with an eluent uniformly across the upper surface of the filling material in a separation column provided with inner structures as disclosed above and packed with a filling material suitable for the separation, the solution is conveyed through the filling material bed, and the fractions containing the desired products are collected from the liquid flow passed through the filling material.

The column and method of the invention have been employed with success in the separation of sucrose and betaine from beet molasses in a column with a diameter of 3.6 m, employing a bed height of 6 m for the separation resin. When an inner structure according to the invention was installed in the column, the separation result improved distinctly as compared with the result achieved with the same column without the inner structures. In that connection, the capacity of said column was compared with the capacity of a smaller column (diameter 2.76 m) with no inner structures. Without the inner structures, the operation of the large separation column was poorer than that of the smaller column. The inner structures enabled the larger column to operate at substantially the same feed capacity as the smaller column. The feed capacity in this connection means the feed quantity of dry solids in a time unit per volume unit of filling material (kg ds/(hm$^3$).

BRIEF DESCRIPTION OF THE DRAWINGS

A preferred embodiment of the column of the invention will now be described with reference to the accompanying drawings, in which.

DESCRIPTION OF THE PREFERRED EMBODIMENTS

Figure 1:
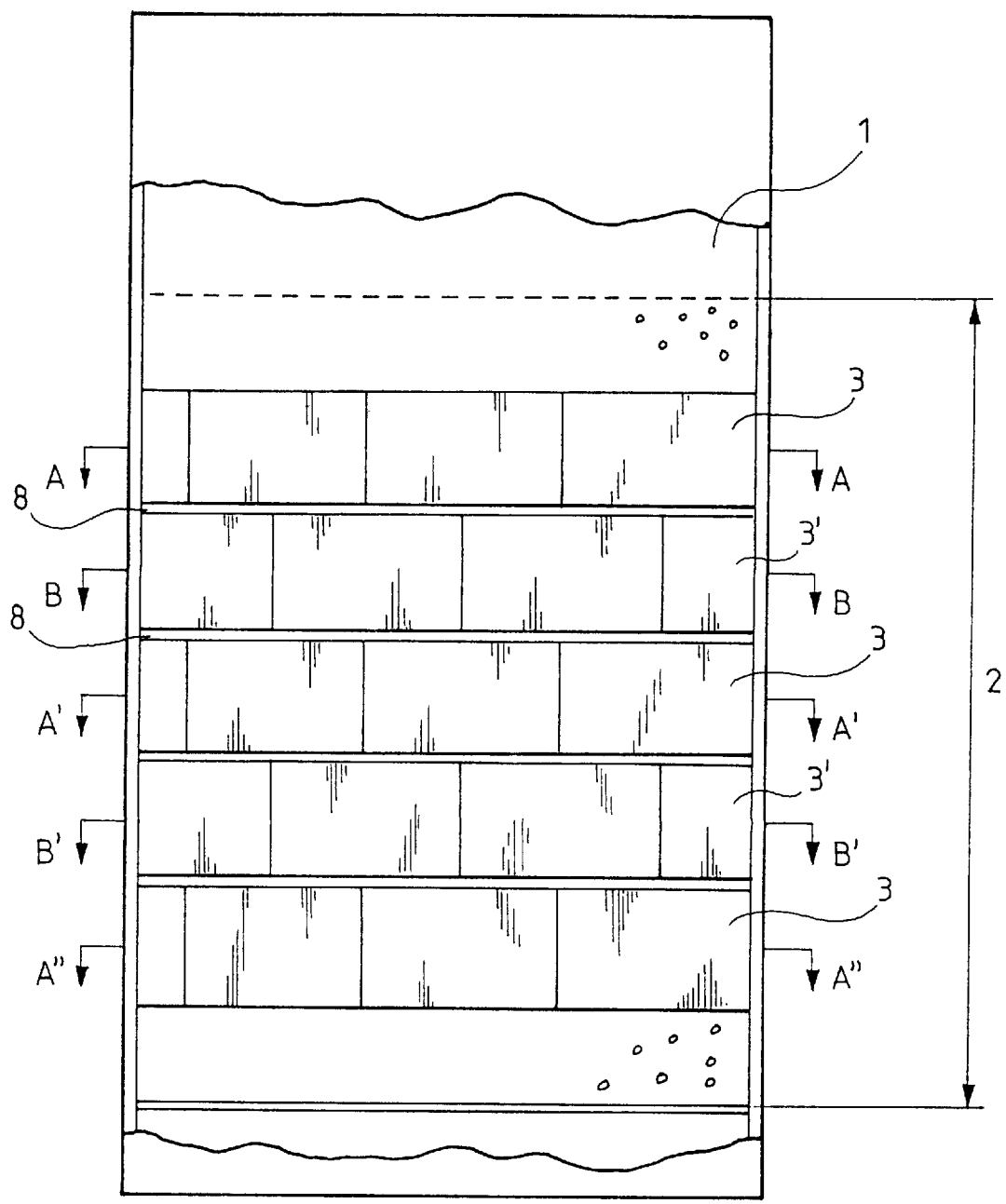
FIG. 1 is a longitudinal section through the axis of a column.

In the embodiment of the invention shown in FIG. 1, the filling material space 2 in column 1 comprises five zones 3, 3'. In succession, the first, third and fifth zone and the second and fourth zone respectively have similar geometries. In this embodiment, zones 3, 3' are of equal height, and a space 8 with no walls 4 and having a height of about 5% of the height of the zone is provided therebetween. The cell structures of two superimposed zones 3, 3' are so arranged that the straight lines 6 at which the walls 4 of a specific zone adjoin are in the middle 7 of the sections 5 of the next zone.

Figure 5:
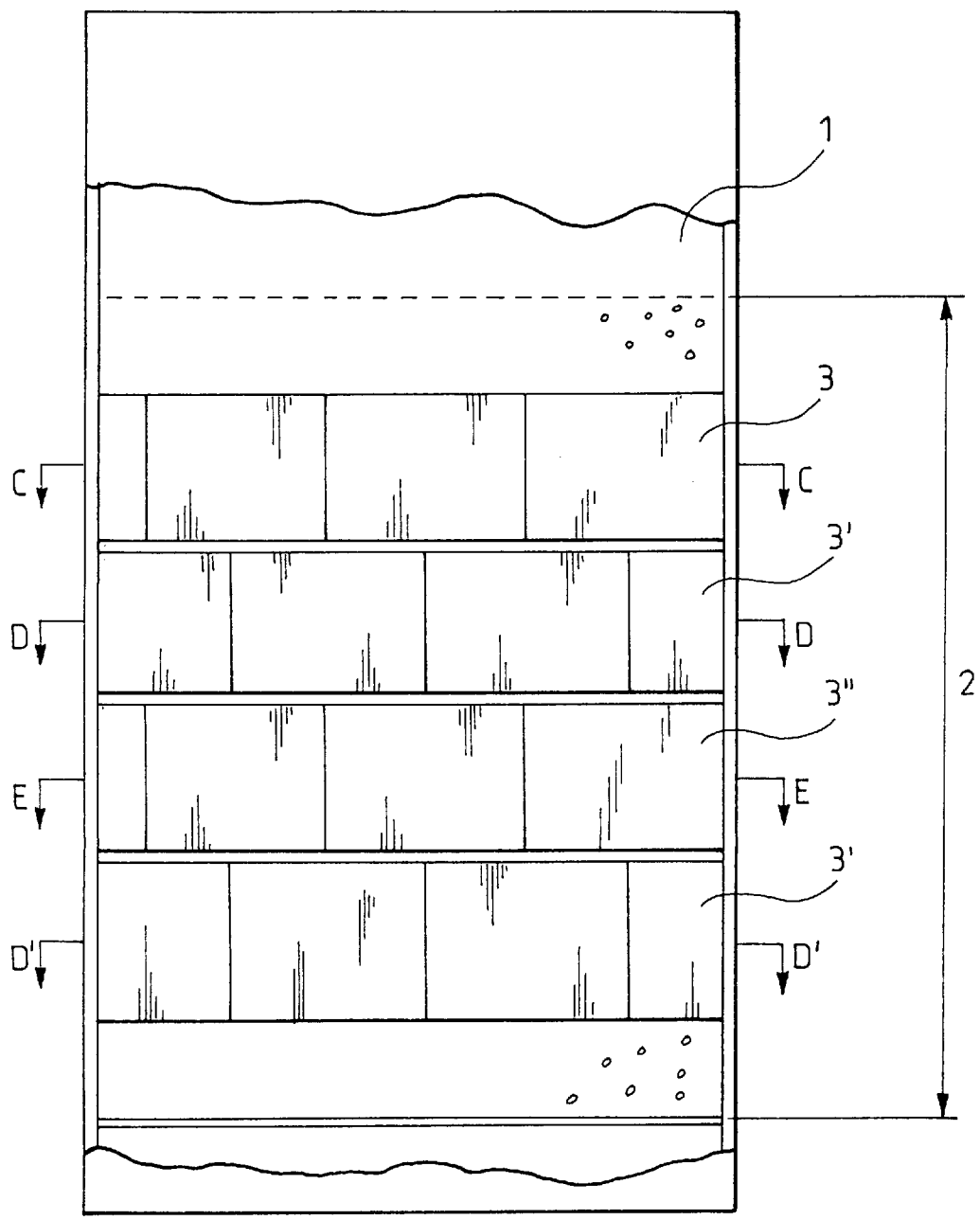
FIG. 5 is a longitudinal section through the axis of a column of another kind.
Figure 6:
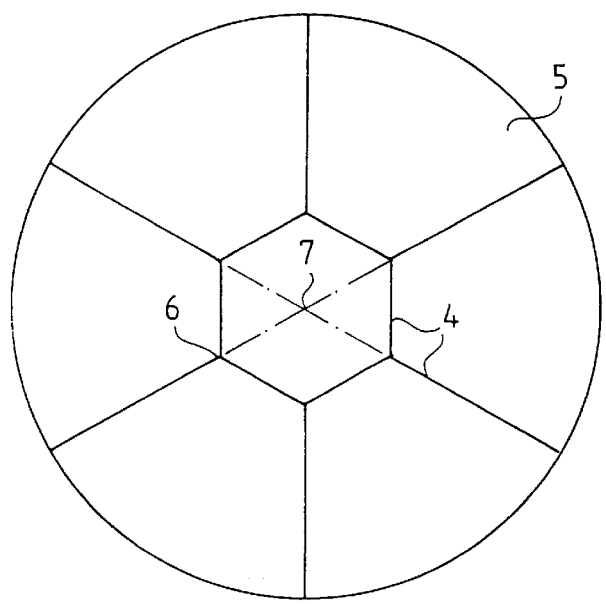
FIG. 6 shows a cross-section of the column of FIG. 5 in plane C—C.
Figure 7:
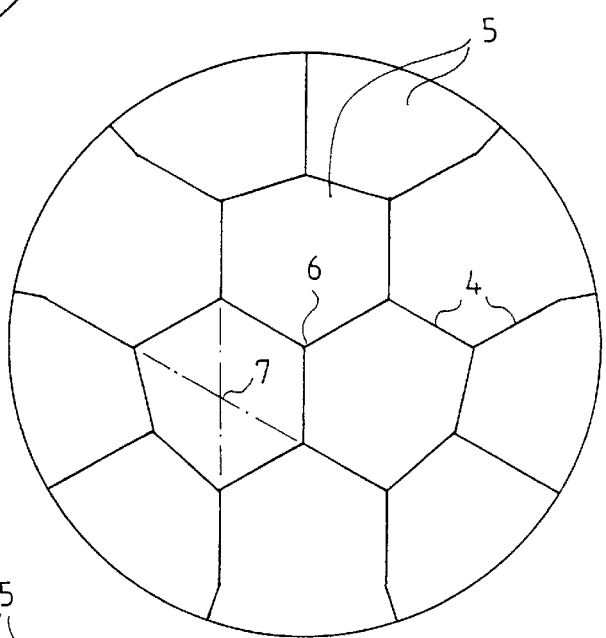
FIG. 7 shows cross-sections of the column of FIG. 5 in planes D—D and D'—D'.
Figure 8:
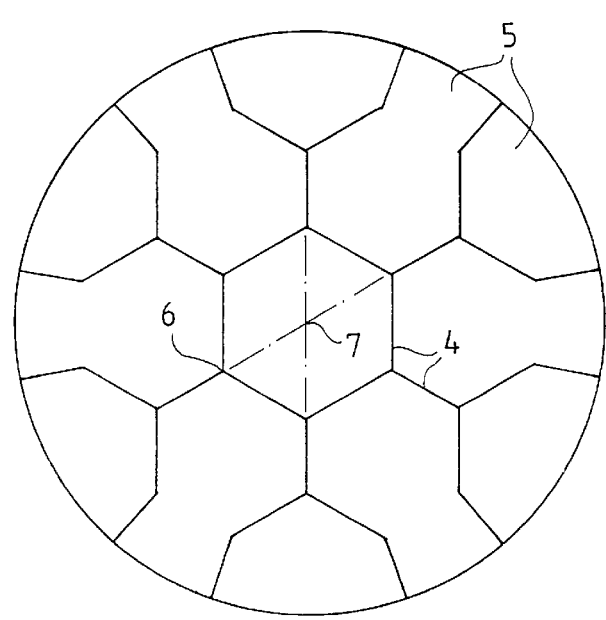
FIG. 8 shows a cross-section of the column of FIG. 5 in plane E—E.

The embodiment of the invention shown in FIG. 5 differs from that shown in FIG. 1 with respect to the cross-sections of different zones and, in addition, in that it contains four zones 3, 3' and 3". The first and third zones from the bottom have similar geometries, and the second and fourth zones differ in their geometry both from one another and from the first and third zones. The inner structures shown in FIGS. 5 to 8 are suitable, for instance, for columns with a diameter of about 3.9 m.

The walls included in the different zones are fixedly attached to one another and to the column wall for instance by welding. The walls may be made from a 2 mm metal sheet, for instance. To avoid possible excessive stresses, structures permitting resilience of the sheet, for example bellows-type structures, may be used in the wall plates.

Above and beneath the filling material space, the column comprises known structures that are necessary for accomplishing the separation process. Such structures have been described for instance in British Patent Specification No. 1,403,382 and U.S. Pat. No. 4,604,199.

The invention and the advantages achieved therewith will be illustrated in further detail by means of the following examples, which are not intended to limit the invention. Examples A and C are reference examples, and the columns employed in them did not contain the inner structures of the invention.

In all examples, sucrose and betaine were separated from beet molasses. In terms of mathematical analysis, 88.0% on dry solids was selected as the purity for the sucrose fraction, 22.0% was selected as the sucrose content of the residual fraction, and a betaine purity of 45.0% was selected for the betaine fraction.

Figure 9:
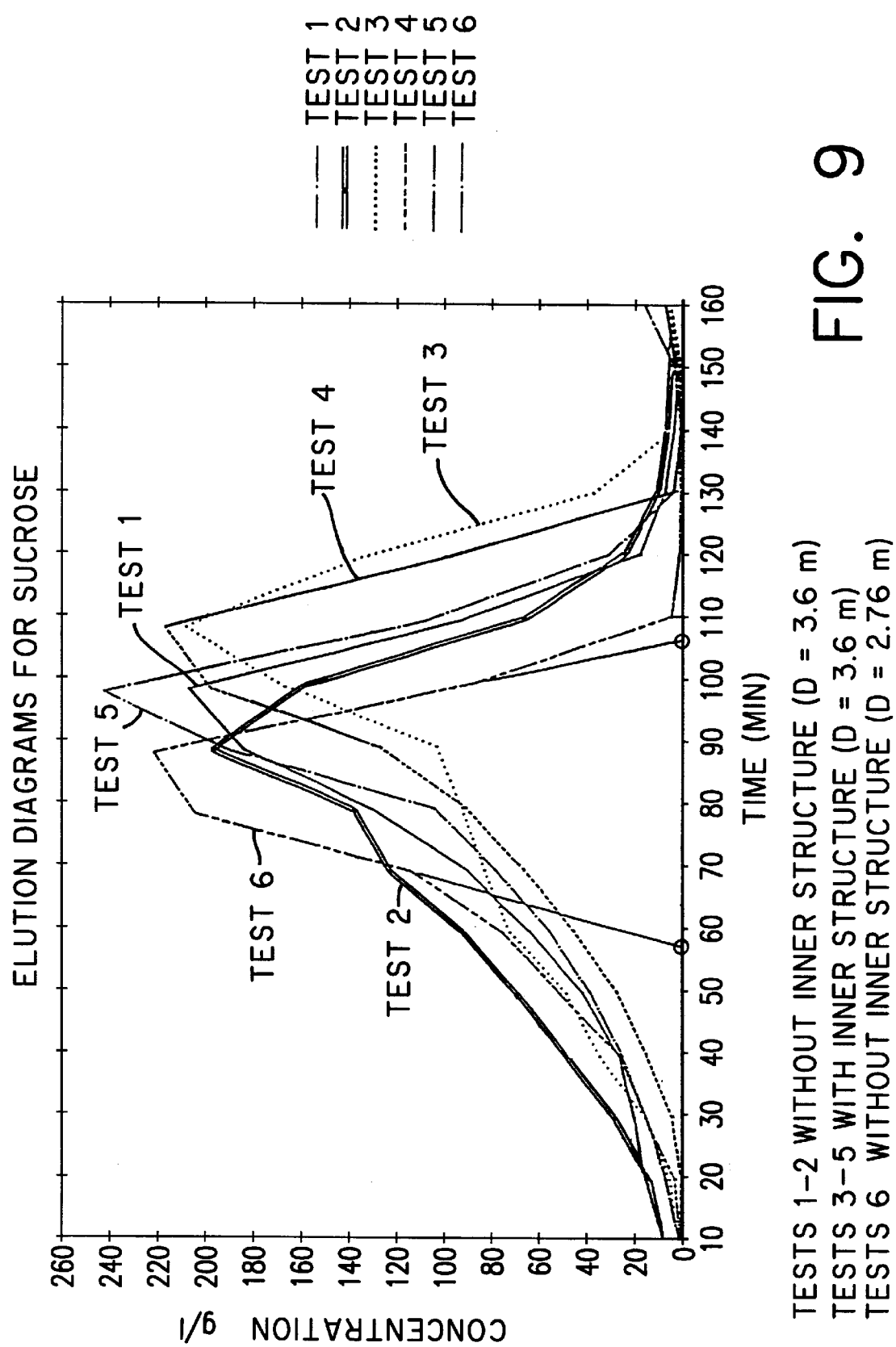
FIG. 9 shows the elution diagrams for sucrose obtained in the examples.

FIG. 9 shows the elution diagrams for sucrose obtained in the examples.

The separation results obtained in the examples were also evaluated by determining the following computational quantities: number of theoretical plates, and height of theoretical transfer unit. These were determined by means of the following known mathematical formulae:

$$N = 16 \, (V/W)^2$$

and $$HETP = L/N$$

wherein
 N=number of theoretical plates
 V=eluting volume (liters) of a peak in the separation diagram
 W=bottom width of the peak (liters)
 HETP=height of theoretical transfer unit (mm)
 L=height of resin bed Analyses of the feed solutions employed in the examples are shown in Table 1.

TABLE 1

Feed solutions employed in the examples

| | Example A | | Example B | | | Example C |
|---|---|---|---|---|---|---|
| | test 1 | test 2 | test 3 | test 4 | test 5 | test 6 |
| sucrose, % of d.s. | 60.88 | 60.08 | 59.57 | 59.73 | 58.56 | 55.52 |
| betaine, % of d.s. | 6.63 | 6.76 | 5.54 | 4.55 | 5.22 | 4.19 |
| monosaccharides, % of d.s. | 1.05 | 0.57 | 0.54 | 0.44 | 2.78 | 0.26 |
| raffinose, % of d.s. | 3.01 | 2.47 | 2.58 | 2.69 | 1.86 | 2.97 |
| others, % of d.s. | 28.43 | 30.12 | 31.77 | 32.59 | 31.58 | 37.06 |
| conductivity, mS/cm | 24.4 | 22.8 | 26.7 | 24.1 | 25.7 | 28.0 |
| pH | 8.7 | 8.5 | 8.7 | 8.7 | 8.5 | 8.9 |
| dry solids content, % by weight | 36.9 | 37.8 | 37.6 | 36.7 | 38.3 | 37.0 | d.s. = dry solids

EXAMPLE A

Diameter of column 3.6 m, no inner structures

Test 1

The filling material employed was a strongly acid cation exchange resin having the following resin analysis:

| make | Duolite |
|---|---|
| capacity | 1.58 equiv./l |
| water retention capacity | 0.95 g H$_2$O/g |
| average spherule size | 0.47 mm |
| divinyl benzene cross-linking grade | 6.5% |

The test conditions were the following:

| bed height | 6.0 m |
|---|---|
| volumetric flow | 9.0 m$^3$/h |
| temperature | 80° C. |
| feed volume | 4650 l |
| dry solids content in feed | 36.9–37.8% by weight |
| feed interval | 160 minutes |

During the separation process, a given quantity (feed volume) of feed solution was supplied across the surface of the separation resin at given intervals (feed intervals); during the intervals between the feeds, water as eluent was passed through the column.

Before the start of Test 1, the separation resin in the column was backwashed, whereafter it was allowed to compact. The feed device was adjusted to the surface of the separation resin, and the run was started. After the processing according to the method had been continued for one day, the feed device was readjusted as accurately as possible to the resin surface. The process was allowed to equalize, and a first series of samples was collected from the separation and the elution diagrams plotted.

Test 2

The processing according to the method started in Test 1 was continued with the same parameters for one week, whereafter another series of samples was taken and the elution diagrams plotted.

In Test 2, the desired purity 45% for the betaine fraction was not achieved, but the purity remained at 43.0%.

Upon comparison of the sucrose elution diagrams for Test 1 and Test 2 shown in FIG. 9, it is to be seen that the posterior slope of the peak has flattened out and the bottom of the peak has broadened.

In Test 2, the number of theoretical plates obtained was N=61, and HETP was 98 mm.

EXAMPLE B

Column diameter 3.6 m, inner structure according to the invention

Test 3

Figure 2:
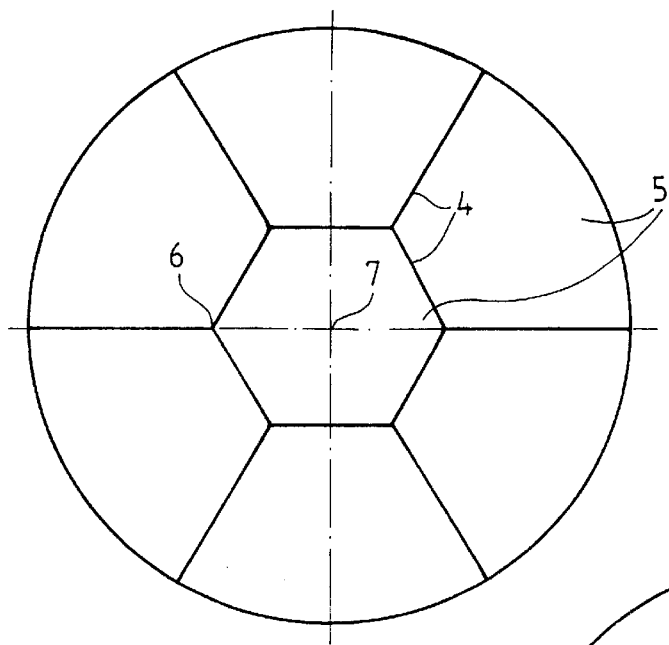
FIG. 2 shows cross-sections of the column of FIG. 1 in planes A—A, A'—A' and A"—A"
Figure 3:
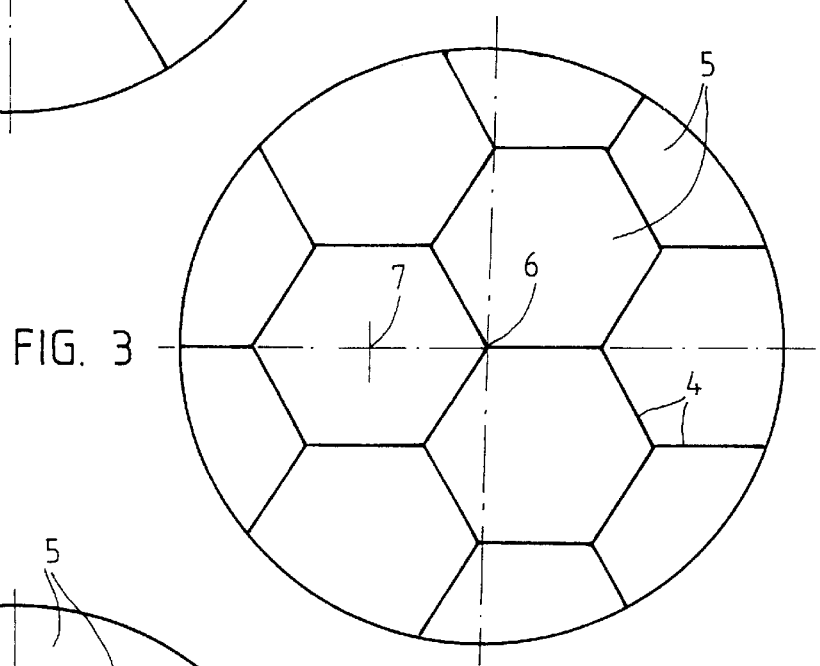
FIG. 3 shows cross-sections of the column of FIG. 1 in planes B—B and B'—B'.
Figure 4:
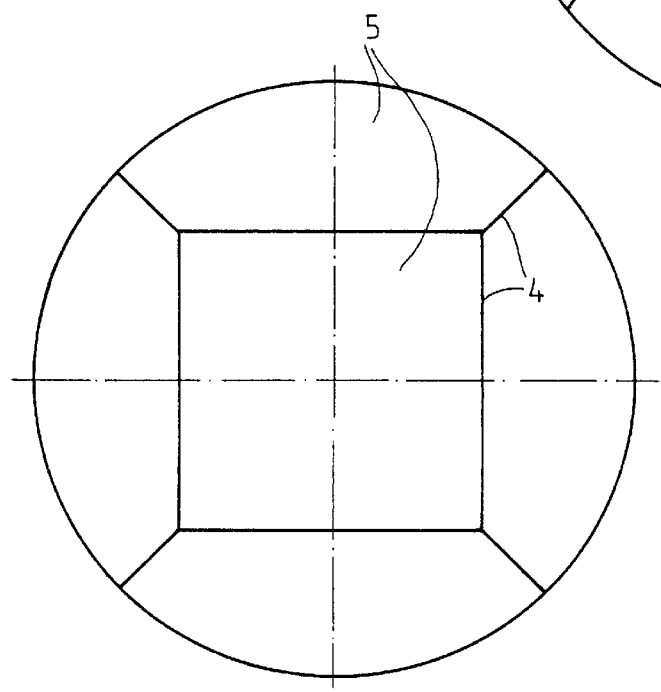
FIG. 4 is a cross-section of a conceivable different cell structure.

After the test carried out in Example A, the column was emptied of separation resin. The cover of the column was removed, and cell structures according to FIGS. 1, 2 and 3 were installed in the column, starting from the bottom of the column. Every second cell structure was alike. The walls of the cell structure were of 2 mm steel sheet, and they were welded to the column wall in such a way that the walls of the cell structures were not aligned but offset. The height of the walls in each cell structure was 1 m. The lowermost cell structure was installed at a height of 0.5 m from the bottom surface of the filling resin bed, and the cell structures were spaced at 50 mm intervals.

The separation resin was pumped back into the separation column and backwashed. Processing with the same parameters as in Tests 1 and 2 was started in the column. The feed interval was 150 minutes. A series of samples was taken one week from the start. On the basis of the results of Tests 2 and 3, it appeared that the separation result achieved using the inner structures was improved (cf. the elution diagrams in FIG. 9). The composition of the feed solutions in Tests 2 and 3 was virtually similar.

Test 4

In Test 4, the feed volume was 4.8 m³. The other process parameters were the same as in Test 3. The process was allowed to equalize for two weeks before sampling.

The feed concentration was 36.7% by weight. The sucrose and betaine yields were lower, and the recycling percentage was higher than in Test 3.

Test 4 provided a distinct improvement in the concentration of the sucrose fraction, which increased from the value 20.2 g/100 ml in Test 3 to the value 24.6 g/100 ml. Upon comparison of the shape of the sucrose peak in Test 4 with the shape of the sucrose peak in Test 2 (cf. FIG. 9), it is to be seen that the peak is higher and has a narrower bottom when the column has an inner structure.

The number of theoretical plates obtained in Test 4 was N=93 and HETP was 65 mm, which also indicates that separation improved in relation to Test 2.

Test 5

The feed volume was 4.65 m³, and the feed interval was 140 minutes. The process was continued without interruption with no backwashing for more than one month, whereafter series of samples were taken.

The sucrose and betaine yields improved in comparison with Test 4. Also the number of theoretical plates increased from 93 obtained in Test 4 to 117 obtained in this test.

The test gave the best result with a column of a diameter of 3.6 m.

EXAMPLE C

Column diameter 2.76 m, no inner structures

Test 6

The resin analysis of the filling material was the following:

| | |
|---|---|
| make | Korela V09 |
| capacity (H⁺) | 1.39 equiv./l |
| water retention capacity (Na⁺) | 1.16 g H₂O/g |
| average spherule size (Na⁺) | 0.50 mm |
| divinyl benzene cross-linking grade | 5.5% |

The test conditions were the following:

| | |
|---|---|
| bed height | 6.0 m |
| volumetric flow | 5.5 m³/h |
| temperature | 80° C. |
| feed volume | 2500 l |
| dry solids content in feed | 37.0% by weight |
| feed interval | 130 minutes |

The concentration for the residual fraction was 7.4 g/100 ml with a sucrose purity of 22% on dry solids. The concentration of the sucrose fraction was 19.7 g/100 ml with a purity of 88.0%, and the number of theoretical plates was N=113.

The calculated comparative results of Tests 2, 5 and 6 are shown in Table 2.

TABLE 2

Calculated comparative results

| | Test 2 D = 3.6 m (no inner structure) | Test 5 D = 3.6 m (inner structure) | Test 6 D = 2.76 m (no inner structure) |
|---|---|---|---|
| feed capac.,d.s. kg/(m³h) | 15.3 | 16.4 | 16.6 |
| yield$_{sucr}$ | 63.6% | 86.7% | 88.3% |
| yield$_{bet}$ | 64.3% | 86.4% | 95.1% |
| conc$_{resid}$ g/100 ml | 5.9 | 5.9 | 7.4 |
| conc$_{sucr}$ g/100 ml | 19.7 | 23.2 | 19.7 |
| conc$_{bet}$ g/100 ml | 4.6 | 5.5 | 5.4 |
| theoretical plates | 61 | 117 | 113 |
| HETP | 98 mm | 51 mm | 53 mm |
| feed interval | 160 min | 140 min | 130 min | d.s. = dry solids

The above yields for sucrose and betaine were determined on the basis of the dry solids removed from the column.

Recycles are not included in the yield. The yields were calculated from the equation:

$$\text{Yield} = \frac{d.s. \text{ quantity of product in product fraction}}{d.s. \text{ quantity of product removed during cycle}}$$

The tests carried out show that the separation result of a large-scale chromatographic separation column can be improved by installing in the column an inner structure according to the invention. The separation capacity of the column was markedly improved on account of the inner structure. The inner structure enabled a column with a diameter of 3.6 m to operate at a feed capacity of 16.4 kg of dry solids/(m³/h), that is, at nearly the same feed capacity as a column with a diameter of 2.76 m, which had a feed capacity of 16.6 kg of dry solids/(m³h).

We claim:

1. A chromatographic separation system comprising: an outer chromatographic separation column and an inner structure for chromatographic use arranged within the chromatographic separation column, the structure comprising at least two zones, which, during operation of the column, are substantially uniformly filled with a column filling material, the zones being located within the filling material space of the column in the vertical direction, between which zones no means that would hinder vertical flow exist and which are divided by means of substantially vertical walls into separate sections, the zones being so dimensioned that the upper edge of the walls in the uppermost zone is below the upper surface of the column filling material in the operating conditions of the column, and the space between zones being relatively low relative to the height of the zone.

2. The chromatographic separation system as claimed in claim 1 wherein the walls in two successive zones are so arranged as to be offset from one another.

3. The chromatographic separation system as claimed in claim 2 wherein the angles formed by the walls with one another and with the column wall are at least about 90°.

4. The chromatographic separation system as claimed in claim 2 wherein the walls included in each zone form a cell structure in which the walls adjoin one another at an angle of 120° and the column wall in the radial direction of the column.

5. The chromatographic separation system as claimed in claim 2 wherein successive zones contact one another.

6. The chromatographic separation system as claimed in claim 1 wherein the angles formed by the, walls with one another and with the column wall are at least about 90°.

7. The chromatographic separation system as claimed in claim 1 wherein the walls included in each zone form a cell structure in which the walls adjoin one another at an angle of 120° and the column wall in the radial direction of the column.

8. The chromatographic separation system as claimed in claim 1 wherein the cell structures of two superimposed zones are so arranged that the straight lines at which the walls of a specific zone adjoin one another are in the middle of the sections of the following zone.

9. The chromatographic separation system as claimed in claim 1 wherein the combined height of the zones is about 70–90% of the height of the filling material in the column.

10. The chromatographic separation system as claimed in claim 1 wherein spaces with no wall structures are provided between the zones.

11. The chromatographic separation system as claimed in claim 10 wherein each of said spaces with no wall structures has a height at the most about 10% of the height of the zone.

12. The chromatographic separation system as claimed in claim 1 wherein the diameter of the column is 1 to 5 m.

13. The chromatographic separation system as claimed in claim 12 wherein the diameters of the sections are 0.25 to 1.5 m.

14. The chromatographic separation system as claimed in claim 13 wherein the height of each zone is 0.5 to 3 m.

* * * * *